United States Patent
Chizat et al.

Patent Number: 5,087,443
Date of Patent: Feb. 11, 1992

[54] EMULSIONS OF ORGANOPOLYSILOXANES CONTAINING A DIESTER FUNCTIONAL GROUP, THEIR APPLICATION IN TEXTILE, COSMETIC AND DERMATOLOGICAL TREATMENT

[75] Inventors: Francois Chizat, Bron; Michel Peignier, L'Arbresle; Jean F. Grollier, Paris; Claude Dubief, Le Chesnay, all of France

[73] Assignee: L'Oreal, Paris, France

[21] Appl. No.: 417,791

[22] Filed: Oct. 4, 1989

[30] Foreign Application Priority Data

Oct. 5, 1988 [LU] Luxembourg ............................ 87360

[51] Int. Cl.$^5$ .................... A61K 7/021; A61K 7/075; A61K 7/09; A61K 7/48
[52] U.S. Cl. ......................................... 424/47; 424/63; 424/70; 424/71; 424/72; 252/DIG. 13; 252/174.15; 514/772; 514/937; 514/938
[58] Field of Search ....................... 424/70, 63, 78, 47; 514/772, 937, 938; 252/DIG. 13, 174.15

[56] References Cited

U.S. PATENT DOCUMENTS

| | | | |
|---|---|---|---|
| 3,824,303 | 7/1974 | Lanzet et al. ...................... | 424/70 X |
| 4,405,469 | 9/1983 | Hafner et al. ...................... | 528/26 X |
| 4,784,844 | 11/1988 | Thimineur et al. .............. | 514/937 X |

FOREIGN PATENT DOCUMENTS 2079300  1/1982  United Kingdom ................ 514/938

Primary Examiner—Thurman K. Page
Assistant Examiner—Susan S. Rucker
Attorney, Agent, or Firm—Marshall, O'Toole, Gerstein, Murray & Bicknell

[57] ABSTRACT

The invention relates to a silicon/water emulsion comprising, in an aqueous medium:
1/ an organopolysiloxane containing a diester functional group containing, per molecule, at least one unit of formula:

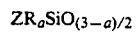

where Z has the formula:

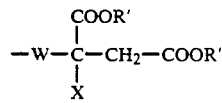

where the symbols R' are $C_1$–$C_{12}$ monovalent saturated hydrocarbon, $C_2$–$C_{12}$ alkoxyalkyl or $C_6$–$C_{12}$ aryl, alkylaryl or arylalkyl radicals, the symbol X is H or $CH_3$, the symbol W is a covalent bond or a $C_1$–$C_4$ alkylene radical, the symbols R are $C_1$–$C_{20}$ alkyl, vinyl, phenyl, 3,3,3-trifluoropropyl or hydroxyl radicals, only one of the radicals R per silicon atom denoting hydroxyl, a is equal to 0, 1 or 2;
2/ an emulsifier chosen from anionic, cationic, amphoteric or nonionic surfactants. Application: to the treatment of textile fibers, to the coating of flexible substrates and to the cosmetic or dermatological treatment of hair or of the skin.

23 Claims, No Drawings

EMULSIONS OF ORGANOPOLYSILOXANES CONTAINING A DIESTER FUNCTIONAL GROUP, THEIR APPLICATION IN TEXTILE, COSMETIC AND DERMATOLOGICAL TREATMENT

The present invention relates to aqueous emulsions of organopolysiloxanes containing a diester functional group. It is the fruit of a cooperation between the L'O-REAL and RHONE-POULENC CHIMIE companies.

The emulsions according to the invention are used for the treatment of synthetic or natural textile fibers, of keratinous fibers such as wool or hair, and for coating flexible substrates, in particular for coating cellulose-based substrates (paper). These emulsions have also been found to be of particular interest in the cosmetic and dermatological treatment of the skin.

The aqueous emulsions in accordance with the invention comprise, in an aqueous medium:
(i) at least one organopolysiloxane containing a diester functional group containing, per molecule, at least one unit of formula:

$$ZR_aSiO_{(3-a)/2} \qquad (I)$$

in which:
Z is a radical of formula:

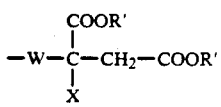

in which:
the symbols R', which are identical or different, are chosen from $C_1$–$C_{12}$ monovalent saturated hydrocarbon radicals, $C_2$–$C_{12}$ alkoxyalkyl monovalent radicals and $C_6$–$C_{12}$ aryl, alkylaryl and arylalkyl radicals;
the symbol X is chosen from a hydrogen atom and the methyl radical;
the symbol W is chosen from a covalent bond and a linear or branched alkylene radical containing from 1 to 4 carbon atoms;
the symbols R, which are identical or different, are chosen from $C_1$–$C_{20}$ alkyl, vinyl, phenyl and 3,3,3-trifluoropropyl radicals, and only one of the radicals R per silicon atom may be a hydroxyl; and
a is chosen from 0, 1 and 2;
(ii) an effective quantity, for forming an emulsion, of at least one emulsifying agent chosen from anionic, nonionic, cationic or amphoteric surfactants or mixtures thereof.

In the units of formula (I), and insofar as the radical Z is concerned, W may be preferably chosen from the following alkylene hydrocarbon radicals:

—CH$_2$— with X = H

—(CH$_2$)$_3$ with X = H

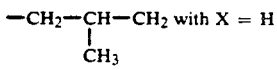

It may also symbolize a single valency bond, and X denotes a methyl.

The radicals R' may be chosen from:

$C_1$–$C_{12}$ alkyl radicals such as methyl, ethyl, n-propyl, isopropyl, n-butyl, 2-ethylhexyl, heptyl and dodecyl radicals;

$C_6$–$C_{12}$ aryl, alkylaryl and arylalkyl radicals such as phenyl, benzyl and tolyl radicals; and $C_2$–$C_{12}$ alkoxyalkyl radicals such as methoxymethyl and ethoxymethyl and 2-methoxyethyl.

The preferred alkyl radicals R are chosen from methyl, ethyl, propyl, n-butyl, n-octyl and 2-ethylhexyl groups. At least 80% of the number of the radicals R are preferably methyl. Only one of the radicals R per silicon atom may be a hydroxyl, in particular in the case where a has the value 2.

The other siloxy units of the organopolysiloxane preferably correspond to the formula:

$$R_bSiO_{(4-b)/2}$$

in which:
R has the same meaning as above and b is equal to 0, 1, 2 or 3.

The organopolysiloxanes containing a diester functional group which are employed according to the invention are preferably linear or cyclic polymers chosen from those of formula:

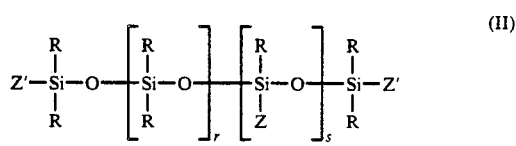

in which:
the symbols R and Z have the meaning given above;
the symbols Z', which are identical or different, are chosen from radicals R and Z;
r is an integer between 0 and 500 inclusive; and
s is an integer chosen between 0 and 50 inclusive and, if s has the value 0, at least one of the two symbols Z' is Z;
and those of formula:

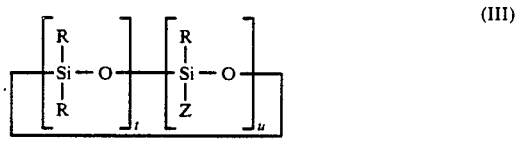

in which:
R and Z have the same meaning as above;
u is an integer between 1 and 20 inclusive;
t is an integer between 0 and 20 inclusive; and
t+u is greater than or equal to 3.

More particular preference is given to random or block polymers containing units of formulae (I), (II) and (III), exhibiting at least one of the following characteristics:
R and R' are methyl;
r is between 5 and 50 inclusive;
s is between 1 and 20 inclusive; and
t+u is between 3 and 10 inclusive.

The organopolysiloxanes containing a diester functional group may be prepared, in particular, according to a process (A).

During a first stage (A$_1$), an organic diester of

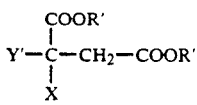   (IV)

or of formula:

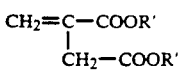   (IV bis)

in which:
Y' is chosen from a linear or branched alkenyl group containing from 2 to 4 carbon atoms inclusive;
R' and X have the same meaning as in formula (I), is added to a hydroorganosilane of formula:

   (V)

in which R and a have the same meaning as in formula (I) above.

This gives an addition product of formula:

   (VI)

in which R, Z and a have the same meaning as in formula (I) above.

The stage (A$_1$) may be performed in bulk or in solution in an organic solvent.

The reaction is exothermic. The operation is generally carried out under reflux of the reaction mixture at a temperature between 60° C. and 140° C. for a period of between 10 minutes and 3 hours.

The silane of formula (V) may be poured onto the diester of formula (IV) and/or (IV bis), or vice versa, or simultaneously.

It is preferable to employ a slight molar excess (of 10% to 50%) of silane of formula (V).

In order to improve the reaction kinetics it is preferable to operate in the presence of a catalyst. The catalysts which may be employed are those employed for performing the hydrosilylation reaction. Those which can be employed in particular are therefore organic peroxides, UV radiations and catalysts based on a metal of the platinum group, in particular platinum, ruthenium and rhodium in a quantity of 10 to 500 ppm (calculated as the weight of metal) relative to the weight of silane of formula (V).

Examples of catalysts which can be mentioned are platinum metal on carbon black, the platinum/olefin complexes described in U.S. Pat. Nos. 3,159,601 and 3,159,662, chloroplatinic acid, chloroplatinous acid, complexes of platinum with a vinylpolysiloxane which are described in U.S. Pat. No. 3,419,593, complexes of platinum of a degree close to zero, which are described in U.S. Pat. Nos. 3,715,334 and 3,814,730 and complexes of platinum with an ethylenically unsaturated organic product, which are described in European Patents EP-A-188,978 and EP-A-190,530.

At the end of reaction, the volatile products are removed by vacuum distillation. A water-pump vacuum of 0.1 to 3 kPa is generally sufficient.

The hydrolysis (or the cohydrolysis) and the polycondensation of a silane of formula (VI) are carried out during a second stage (A$_2$).

This hydrolysis or cohydrolysis and polycondensation may be carried out preferably in a liquid aqueous phase in an acidic medium (preferably HCl) or in a basic medium (preferably NH$_4$OH) or in a solvent medium under conditions which are similar to those of the hydrolysis of chlorosilanes, such as described on pages 193 to 200 of Noll's work "Chemistry and Technology of Silicones", Academic Press (1968).

The concentration of acid or of base in water is generally between 10% and 30% by weight. The hydrolysis medium always contains at least 2 moles of water per mole of silane, generally from 10 to 100 moles of water. The hydrolysis can be carried out continuously or noncontinuously at ambient temperature (20° C.) or at a temperature of between 5° C. and 90° C. The hydrolysis can be carried out at a pressure equal to or higher than atmospheric pressure, continuously or noncontinuously with reinjection of water, at least in the case of the continuous process, to maintain a uniform aqueous phase.

In order to obtain the polymers of formulae (II) and (III) or mixtures thereof, the silanes of formula (VI) in which a = 1 are hydrolized and polycondensed in the optional presence of a dichlorodiorganosilane of formula:

   (VII)

in which R has the definition given in formula (I) above.

The polycondensation can be stopped merely by neutralizing the reaction mixture. In this case, the polymers of formula (II) which are obtained are blocked at each of their ends by a hydroxyl (silanol) group or by the R$_2$ZSiO$_{0.5}$ unit if the silane R$_2$ZSiCl is employed.

The polycondensation can also be stopped by adding an organosilicon compound capable of reacting with the hydroxyl end groups, such as the products of formula:

in which the radicals R have the meaning given in formula (I) above.

The hydrolysis period may be between a few seconds and several hours.

After hydrolysis, the aqueous phase is separated from the siloxane phase by any suitable physical means, generally by phase separation and extraction with an organic solvent such as isopropyl ether.

The siloxane phase can be subsequently washed with water and then optionally distilled to separate the linear polymers of formula (II) from the cyclic polymers of formula (III).

To prepare the polymers of formulae (I), (II) and (III), it is also possible, according to a second process (B) starting with the corresponding polymer, in which all the radicals Z and optionally Z' are hydrogen atoms, and by a hydrosilylation reaction, to add a diester of formulae (IV) or (IV bis) which are defined above.

This polymer is called a polymer containing SiH in what follows: the SiH groups can be present in the chain and/or at the chain ends. These polymers containing SiH are products which are well known in the silicones industry and are generally available commercially.

They are described, for example, in U.S. Pat. No. 3,220,972, U.S. Pat. No. 3,697,473 and U.S. Pat. No. 4,340,709.

This polymer containing SiH can therefore be denoted by the formula:

$$Y-\underset{R}{\overset{R}{\underset{|}{Si}}}-O-\left[\underset{R}{\overset{R}{\underset{|}{Si}}}-O\right]_r\left[\underset{H}{\overset{R}{\underset{|}{Si}}}-O\right]_s\underset{R}{\overset{R}{\underset{|}{Si}}}-Y \quad \text{(VIII)}$$

in which R, r and s have the meaning given above for formula (II), and the radicals Y, which are identical or different, are chosen from the radicals R and a hydrogen atom;

and the formula:

$$\left[\underset{R}{\overset{R}{\underset{|}{Si}}}-O\right]_t\left[\underset{H}{\overset{R}{\underset{|}{Si}}}-O\right]_u \quad \text{(IX)}$$

in which R, t and u have the meaning given above for formula (III).

As in stage (A$_1$) of the process (A), the process (B) employs, therefore, a similar hydrosilylation reaction and it is desirable to perform this reaction with the same catalysts as those indicated in the stage (A$_1$).

This reaction can be performed in bulk or in an organic solvent at a temperature between the normal temperature (25° C.) and 170° C.

The volatile products are removed at the end of reaction by vacuum distillation and/or by extraction.

The process (A) makes it possible to obtain polymers of formula (II) containing hydroxyl end groups and polymers of formulae (II) and (III) containing radicals R some of which may by vinyl radicals.

The process (B) makes it possible to have polymers of well-defined structure by choosing the initial polymers containing SiH.

These diorganopolysiloxanes containing a diester functional group generally take the form of more or less viscous oils, with a viscosity of between 2 and 500,000 mPa s, preferably between 5 and 5000 mPa s at 25° C.

As products of formula (IV), it is preferred more especially to employ:

diesters of optionally α-methylated allylsuccinic or methallylsuccinic acid (formula IV) in which Y' is the CH$_2$=C—CH$_2$— or CH$_2$=C(CH$_3$)—CH$_2$— group; X is H or CH$_3$).

The modified orqanopolysiloxanes obtained by the above processes (A) and (B) are also described in U.S. Pat. No. 4,207,246, U.S. Pat. No. 4,322,473 and U.S. Pat. No. 4,405,469, which are mentioned as references;

diesters of itaconic acid (formula IV bis); two isomeric forms of radicals Z are then obtained:

—CH$_2$CH(COOR')CH$_2$COOR' (formula I: W is —CH$_2$—, X is H); and

—C(CH$_3$)(COOR')CH$_2$COOR' (formula I: W is a valency bond and x is methyl).

The emulsions according to the present invention are of the silicone-in-water type (silicone/water emulsion). The surface-active agents which can be employed in accordance with the invention are described, for example, in U.S. Pat. No. 2,891,920, U.S. Pat. No. 3,294,725, U.S. Pat. No. 3,360,491, U.S. Pat. No. 3,983,148 and FR-A-2,605,634, which are mentioned as references.

The silicone/water emulsions according to the invention preferably comprise:

100 parts by weight of an organopolysiloxane containing a diester functional group, chosen from those of formula (I), (II) and (III) above;

1 to 300 parts by weight of at least one surface-active agent chosen from anionic, cationic, nonionic and amphoteric surface-active agents; and 5 to 2000 parts by weight of water.

The anionic surface-active agents are chosen from alkali metal alkylbenzenesulphonates, alkali metal alkyl sulphates, alkali metal alkyl ether sulphates, alkali metal alkylaryl ether sulphates and alkali metal dioctylsulphosuccinates.

The cationic surface-active agents employed in accordance with the invention are chosen from quaternary ammonium halides such as dialkyl(C$_{10}$–C$_{30}$)dimethylammonium, alkyl(C$_{10}$–C$_{30}$)trimethylammonium or alkyl(C$_{10}$–C$_{30}$)benzyldimethylammonium halides and polyethoxylated quaternary ammonium salts.

The amphoteric surface-active agents employed in accordance with the invention are chosen from N-alkyl-(C$_{10}$–C$_{22}$)betaines, N-alkyl(C$_{10}$–C$_{22}$)sulphobetaines, N-alkyl-(C$_{10}$–C$_{22}$)amidobetaines, alkyl(C$_{10}$–C$_{22}$)imidazolines and asparagine derivatives.

The nonionic surface-active agents are chosen from polyethoxylated fatty acids, sorbitan esters, polyethoxylated sorbitan esters, polyethoxylated alkylphenols, polyethoxylated fatty alcohols, polyethoxylated or polyglycerolated fatty amides and polyglycerolated. alcohols and alpha-diols.

Various processes can be employed to prepare the silicone/water emulsion.

According to a first process, the organopolysiloxane containing a diester functional group is mixed with the surface-active agent, it being possible for the latter to be already in aqueous solution, and water is then added next, if necessary. The whole is then converted into a fine and homogeneous emulsion by being put through a conventional colloid mill. This first process is employed, for example, in patents FR-A-2,064,563, FR-A-2,094,322, FR-A-2,114,230 and EP-A-169,098.

According to a second process, the surface-active agent and at least a part of the water are premixed at a temperature between the ambient temperature (25° C.) and 80° C. until a homogeneous mixture is obtained, and the organopolysiloxane is then added slowly to the premix, while stirring vigorously at a temperature of between 25° C. and 80° C. The consistency of the homogeneous emulsion obtained is regulated by adding water if necessary. This second process is described, for example, in French Patents FR-A-2,471,210 and FR-A-2,485,923.

The Applicant has found that the silicone/water emulsions in accordance with the present invention and prepared according to the two processes described above imparted, surprisingly, an improved softness to natural and synthetic textile fibers and to keratinous fibers.

A subject of the present invention consists of the use of the silicone/water emulsions such as defined above for the treatment of synthetic or natural textile fibers and of keratinous fibers and for coating flexible substrates, in particular for coating cellulose-based substrates such as paper.

These emulsions can, furthermore, be employed in cosmetics and endow hair with particularly surprising properties of disentangling and of softness, and an improved softness to the skin.

The emulsions which are particularly preferred for the use in cosmetics according to the invention comprise a diorganopolysiloxane containing a diester functional group defined above, in combination with a quaternary ammonium halide.

Another subject of the invention consists, therefore, of a composition in the form of an aqueous emulsion intended for the treatment of hair or of the skin in cosmetics and/or in dermatology, comprising a diorganopolysiloxane containing a diester functional group and a quaternary ammonium halide comprising at least one $C_{10}$-$C_{30}$ fatty chain.

A dialkyl($C_{10}$-$C_{30}$)dimethylammonium halide or alkyl($C_{10}$-$C_{30}$)trimethylammonium halide is preferably employed.

Distearyldimethylammonium chloride and behenyltrimethylammonium chloride are more particularly employed.

These aqueous emulsions based on a diorganopolysiloxane containing a diester functional group and on a quaternary ammonium halide can be prepared according to the processes described above or according to a process consisting in diluting a mixed melt of this combination in water or in water heated to a temperature of 70° C. to 100° C., with stirring.

The mixed melt is prepared by heating the mixture of the two components of the combination which are defined above to a temperature slightly above the melting point. This temperature is preferably close to 90° C.

With a view to producing the mixed melt, the weight proportions of each of the compounds may be between 2.5% and 97.5% relative to the total weight of the mixed melt.

The aqueous emulsion is obtained by diluting the mixed melt progressively with stirring, with two to ten times, and preferably four to six times, its weight of hot water, at a temperature which is also close to the melting point of the two components of the combination and preferably at approximately 90° C.

The aqueous emulsion thus obtained is particularly stable with time and is subsequently easily diluted with cold water.

The cosmetic treatment compositions containing the stable aqueous emulsion in accordance with the invention and containing at least one organopolysiloxane containing a diester functional group chosen from those of formulae (I), (II) and (III) above are intended more particularly to be applied to hair or to the skin. In their preferred embodiment they contain the quaternary ammonium halide in proportions of between 0.01% and 15% by weight and preferably between 0.02% and 10% by weight relative to the total weight of the composition and the diorganopolysiloxane containing a diester functional group comprising, per molecule, one unit of formula (I) in proportions of between 0.01% and 15% by weight and preferably between 0.02% and 10% by weight.

These compositions may also include a solvent and, more particularly, a $C_1$-$C_4$ alcohol and may be presented in a thickened or unthickened form, as a cream or a gel and may be pressurized in an aerosol in the form of foams and of sprays.

They may be employed more particularly as a shampoo, as a conditioning composition, as rinsing products which can be applied after shampooing, before or after dyeing and bleaching, before or after permanent-waving or straightening, as hair-setting or blow-drying lotions, as restructuring compositions or as additives to permanent-waving or as skin care compositions.

They may also be employed in dermatology, in which case they contain a dermatologically active substance.

The compositions in accordance with the invention may contain any other adjuvants usually employed in cosmetics, such as perfumes, colorants, preserving agents, hydrating agents, sequestering agents, filtering agents, foaming agents, such as surface-active agents and foaming polymers, conditioning agents, such as, for example, polymers and, in particular, cationic, anionic, nonionic or amphoteric polymers or mixtures thereof, thickening agents, foam stabilizers, propellants or other adjuvants usually employed in compositions for hair or the skin, depending on the intended application.

A preferred embodiment consists in combining a cationic polymer and an anionic polymer in the composition. The anionic polymer may be chosen from polymers derived from carboxylic acids such as, for example, acrylic or methacrylic acid, from maleic acid or anhydride, or from crotonic acid. The cationic polymer preferably contains a large number of primary, secondary, tertiary or quaternary amine groups and is chosen more particularly from cellulose-based cationic polymers. The polymers have a molecular weight which is generally between 500 and 3,000,000.

Such polymer combinations are described, among others, in French Patent 2,383,660.

Their pH is generally between 3 and 10. It can be adjusted with the aid of alkalifying or acidifying agents which are well known in the art in the field of cosmetics.

The thickeners may be chosen from xanthan gums, guar gum or its derivatives, gum arabic or carob gum, sodium alginate, cellulose derivatives, and polyacrylic acid derivatives. These compositions may also be thickened with a mixture of phosphoric ester and of amide or with a product resulting from the ionic interaction of a cationic polymer consisting of a copolymer of cellulose or of a cellulose derivative grafted with a quaternary ammonium salt of a water-soluble monomer and of a carboxylic anionic polymer with an absolute capillary viscosity lower than or equal to $30 \times 10^{-3}$ Pa s in dimethylformamide or methanol at a concentration of 5% and at 30° C., as described more particularly in French Patent No. 2,598,611.

These thickeners are preferably employed in proportions of between 0.1% and 30% by weight, and in particular between 0.2% and 15% by weight relative to the total weight of the composition.

The propellent agents are conventional propellants such as, more particularly, alkanes, fluoroalkanes, chlorofluoroalkanes or mixtures thereof.

The cosmetic treatment process employing the emulsion such as defined above consists essentially in applying the composition either to hair according to the intended usage (shampoo, rinsing treatment, unrinsed hair styling treatment), or to the skin (bath, shower, suntanning products, shaving products, perfumed lotions, creams or milk).

The following examples are intended to illustrate the invention without, however, being of a limiting nature.

The reference examples are intended to illustrate the preparation of the compounds employed in the combination in accordance with the invention.

REFERENCE EXAMPLE 1

907 g, that is 5.74 moles of methyl itaconate and 129 mg of chloroplatinic acid ($H_2PtCl_6$) are charged into a 2-liter three-necked reactor fitted with a condenser, a stirrer and a dropping funnel.

The temperature is raised to 116° C. and 792.5 g (6.89 moles) of $CH_3HSiCl_2$, that is a 20% molar excess relative to the itaconate, are then run in over 65 minutes.

Since the reaction is exothermic, the temperature stays in the region of 120° C. without any additional heat input. When the addition is finished, the temperature is 112° C. The reaction temperature is kept at reflux for 1 hour 50 minutes and the excess $CH_3HSiCl_2$ is then distilled off and 1274 g of a liquid adduct are obtained, whose boiling point is 80° C. at 0.13 kPa. The weight yield of the adduct is 71%.

NMR analysis of the adduct shows that it contains approximately 60 mol % of radicals:

$CH_2CH(COOCH_3)CH_2COOCH_3$ and 40 mol % of radicals:

$C(CH_3)(COOCH_3)CH_2COOCH_3$.

REFERENCE EXAMPLE 2

Preparation of a compound of formula (II) in which $R=CH_3$, the two end radicals $R=OH$; $Z'=Z=$mixture of radicals $—CH_2—CH(COOCH_3)CH_2COOCH_3$ and $—C(CH_3)(COOCH_3)CH_2COOCH_3$; $r=0$; $s=6.6$ (statistical mean value).

340 g of an aqueous solution of ammonia (20% by weight of $NH_4OH$) and 370 ml of water are charged into the same three-necked reactor as that employed in Example 1. 500 g (1.83 moles) of the adduct obtained in Example 1, dissolved in 500 ml of isopropyl ether, are run in over 50 minutes, the temperature being maintained at 25° C.

At the end of hydrolysis the mother liquors are separated off and 500 ml of isopropyl ether are added again to promote the phase separation. The organic solution separated off is washed again with water, is dried and is devolatilized up to a temperature of 100° C. under a vacuum of 2 kPa.

323 g of a clear oil are then obtained, having a hydroxyl group weight content of 1.8%, a viscosity of 35 mPa s at 25° C. and an ester functional group weight percentage of 54.2%.

REFERENCE EXAMPLE 3

Preparation of a compound of formula (II) in which $R=CH_3$, $Z'=OH$; $Z=$mixture of radicals $—CH_2CH(COOCH_3)CH_2COOCH_3$ and $—C(CH_3)(COOCH_3)CH_2COOCH_3$, r represents a statistical mean value equal to 40 and s represents a statistical mean value equal to 2.

2800 g of water are charged into a 10-liter three-necked reactor and 903 g (7 moles) of $(CH_3)_2SiCl_2$ and 98 g (0.35 moles) of the adduct obtained in Example 1 are run in over one hour. The temperature rises gradually from 25° C. to 65° C. during the addition. After the addition the reaction mixture is kept stirred for 30 minutes and the acidic waters are separated off. 350 ml of isopropyl ether are added and the ether solution is washed three times and concentrated, firstly up to 100° C. at atmospheric pressure and then up to 80° C. under a vacuum of 2.5 kPa.

456 g of clear and colorless oil are then obtained, having the following characteristics:

| | |
|---|---|
| viscosity at 25° C. | 20 mPa.s |
| % (by weight) of hydroxyl | 1% |
| weight percentage of ester functional group | 4.8% |
| weight yield of oil | 77% |

REFERENCE EXAMPLE 4

Preparation of a compound of formula (II) in which $Z'=R=CH_3$, $Z=$mixture of radicals $—CH_2—CH(COOCH_3)CH_2COOCH_3$ and $—C(CH_3)(COOCH_3)CH_2COOCH_3$; $r=31$ (exact value); $s=17$ (exact value).

Into a 5-liter three-necked reactor are charged 816 g of an oil of formula:

$(CH_3)_3SiO(CH_3HSiO)_{17}[(CH_3)_2SiO]_{31}Si(CH_3)_3$ and 948 g of methyl itaconate, the whole in 1540 g of xylene, together with chloroplatinic acid in such quantity that there are approximately 150 ppm of platinum metal relative to the weight of siloxane polymer. The temperature is raised to 145° C. and this is maintained for 24 hours. Xylene and excess methyl itaconate are then distilled off by heating to 140° C. under a vacuum of 2.5 kPa.

1370 g of a clear and colorless oil are then obtained, with a viscosity of 950 mPa s and an ester functional group weight percentage of 28.2%.

REFERENCE EXAMPLE 5

The following are charged simultaneously into a one-liter reactor fitted with a condenser and a stirrer:

174 g, that is 1.1 moles of methyl itaconate, 46 g of a cyclic hydromethylsiloxane of 92% purity of formula:

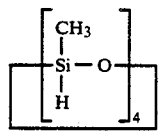

25 mg of $H_2PtCl_6 \cdot 6H_2O$

The reaction mixture is heated to 135° C. and the temperature is maintained between 135° C. and 160° C. for 1 hour 30 minutes.

The excess methyl itaconate is distilled off by heating the reaction mixture to 160° C. at 0.133 kPa. 146 g of devolatilized oil are obtained, orange-yellow in color, with a viscosity of 2240 mPa s at 25° C., in which the weight percentage of ester is 50%.

The mass spectrum and the IR spectrum ($CHCl_3$) confirm that the oil obtained is indeed the product of formula:

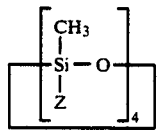

Z being an itaconyl radical.

Examples 6 to 12 below illustrate emulsions which can be employed in the treatment of textiles. The silicone oil prepared in reference Example 3 is employed in these examples.

ANIONIC EMULSIONS

EXAMPLE 6

Surfactant: sodium lauryl sulphate 25 g of silicone oil and 2.5 g of Na lauryl sulphate are placed in a 100-ml beaker. 4.5 g of distilled water are introduced slowly with moderate stirring using the ultra Turrax ®, then the speed of the Turrax ® is increased to 10,000 rev/min. When the temperature reaches 65° C. to 70° C. there is a large increase in viscosity and a thick phase is obtained which is gradually diluted using 18 g of distilled water.

The emulsion obtained has a mean particle size of 0.25 μm. It is stable with time.

EXAMPLE 7

Surfactant: dioctylsulphosuccinate 2.17 g of dioctylsulphosuccinate (70% solids content) and 15.12 g of silicone oil are placed in a 100-ml beaker. When stirred, the whole forms a homogeneous solution. It can be seen that this solution does not form an emulsion spontaneously if added dropwise to magnetically stirred distilled water.

When stirred with the ultra Turrax ® and when distilled water is introduced progressively, there is a progressive increase in viscosity and the whole becomes white when 6.58 g of water have been added. Finally, a dilution using 10.71 g of distilled water is effected and a stable emulsion is obtained, whose mean particle size is 0.32 μm.

NONIONIC EMULSIONS

EXAMPLE 8

Surfactant: ethoxylated nonylphenol 1.42 g of Cemulsol NP 5 ® (ethoxylated nonylphenol containing 5 ethylene oxide units) are placed in a 100-ml beaker, followed by 1.63 g of Cemulsol NP 9 ® (ethoxylated nonylphenol containing 9 ethylene oxide units) and 5.62 g of distilled water. A thick phase is obtained on stirring, into which 34.5 g of silicone oil are introduced progressively with stirring using the ultra Turrax ®. This mill base is then diluted with 28 g of distilled water while being gently stirred.

The emulsion thus obtained has a mean particle size of 1.25 μm. After a few days this emulsion exhibits a clear phase at the bottom of the flask.

EXAMPLE 9

Surfactant: polyglycerolated dodecanediol (containing 3 glyceryl units)

2.66 g of polyglycerolated dodecanediol (containing 3 glyceryl units) and 24.4 g of silicone oil are placed in a 100-ml beaker. Distilled water is introduced with stirring using the ultra Turrax ®. No thick phase forms, but there is a sudden inversion when 11.2 g of water have been added. The corresponding emulsion is stable but it is difficult to get rid of bubbles. The mean particle size is 0.88 μm.

CATIONIC EMULSIONS

EXAMPLE 10

The emulsion is produced as in Example 9 with the following as surfactants:

| | |
|---|---|
| Cemulsol NP 9 ® (oxyethylenated nonylphenol with 9 EO) | 1.02 g |
| Cemulsol NP 5 ® (oxyethylenated nonylphenol with 5 EO) | 0.48 g |
| Cequartyl A ® with a solids content of 50% (dodecyl-benzyldimethylammonium chloride) | 1.00 g |
| Silicone oil | 20.17 g |

Phase inversion occurs with 10.5 g of distilled water using the ultra Turrax ®. The mean particle size is 0.75 μm.

SUBSTANTIVITY TEST

An approximately 3 g piece of dyed cotton knit, approximately 240 g/m$^2$ in weight, is taken. After washing with a product based on sodium dodecylbenzenesulphonate to ensure that it is of an anionic nature and rinsing, this article is put in a 300-ml beaker containing 140 ml of distilled water acidified to pH 4 with acetic acid and 0.1 g of the above emulsion. Heating is applied to raise the temperature by 1° C. per minute with magnetic stirring. When the temperature reaches 42° C. the bath is completely exhausted (perfectly clear), and this has required about twenty minutes.

The sample thus treated is dried at 70° C. Its handle is softer than that of the control.

EXAMPLE 11

The method followed is as in Example 10, except that the surfactant employed is Cequartyl A ® with a solids content of 50%, employed in a proportion of 3.72 g of surfactant per 15.20 g of silicone oil.

The substantivity test shows that this emulsion is more substantive than the preceding one, since bath exhaustion takes place already at 36° C.

EXAMPLE 12

The method followed is as in Example 10. The mixture to be emulsified has the following composition:

| | |
|---|---|
| 25% strength solution of Cemulcat C ® acetate (copra amine) | 3.66 g |
| Cemulsol NP 5 ® | 1.09 g |
| Silicone oil | 15.20 g |

The phase inversion takes place when 6 g of water have been added.

The emulsion is bubbly even after the addition of 7 g of water.

Its substantivity is good (40° C.).

Examples 13 to 23 below illustrate cosmetic compositions containing the aqueous emulsion based on an organopolysiloxane containing a diester functional group and a quaternary ammonium halide.

EXAMPLE 13

A hair rinse lotion for applying to hair after a shampoo, of the following composition, is prepared:

| | |
|---|---|
| Aqueous emulsion containing 20% of AS obtained by dilution with hot water of a mixed melt of 50/50 by weight of distearyldimethylammonium chloride and | 2.0 g |

| | |
|---|---|
| of diorganopolysiloxane containing a dimethyl itaconate functional group of Reference Example 3 | |
| (that is, as distearyldimethylammonium chloride | 0.2 g AS |
| and as diorganopolysiloxane | 0.2 g AS) |
| Water q.s. | 100.0 g |

On wet, especially bleached permanent-waved, hair, this lotion produces a remarkable improvement in disentangling when compared with a lotion containing only distearyldimethylammonium chloride.

It makes dry or wet hair very soft throughout its length. The dried hair is very shiny, keeps its bounce and exhibits no static electricity.

EXAMPLE 14

A hair conditioner of the following composition is prepared:

| | |
|---|---|
| Aqueous emulsion containing 20% of AS obtained by diluting with hot water a 50/50 by weight mixed melt of behenyl-trimethylammonium chloride and of diorganopolysiloxane containing a dimethyl itaconate functional group of Reference Example 3 | 2.0 g |
| (that is, as behenyltrimethylammonium chloride | 0.2 g AS |
| and as diorganopolysiloxane | 0.2 g AS) |
| Hydroxypropylated and quaternized guar gum sold by Celanese under the name Jaguar C 13 S | 1.0 g |
| Perfume, preserving agent, colorant q.s. | |
| Triethanolamine q.s. | pH = 6.8 |
| Water q.s. | 100.0 g |

This composition is applied to washed and roughly dried hair. After rinsing, the wet hair disentangles very easily. The dried hair is bouncy, shiny and very soft.

EXAMPLE 15

A hair rinse lotion to be applied to hair after a shampoo, of the following composition, is prepared:

| | |
|---|---|
| Aqueous emulsion containing 20% of AS obtained by diluting with hot water a 50/50 by weight mixed melt of distearyl-dimethylammonium chloride and of diorganopolysiloxane containing a dimethyl itaconate functional group of Reference Example 3 | 4.0 g |
| (that is, as distearyldimethylammonium chloride | 0.4 g AS |
| and as diorganopolysiloxane | 0.4 g AS) |
| Condensate of epichlorohydrin with the condensate of adipic acid and of diethylenetriamine, prepared according to Example (Ia) of French Patent 2,252,840 | 1.0 g AS |
| Perfume, preserving agent, colorant q.s. | |
| Hydrochloric acid q.s. | pH = 8.5 |
| Water q.s. | 100.0 g |

This composition makes wet hair easier to disentangle and endows dried hair with fullness and bounce.

EXAMPLE 16

A hair conditioning rinse, of the following composition, is prepared:

| | |
|---|---|
| Aqueous emulsion containing 20% of AS obtained by diluting with hot water a 50/50 by weight mixed melt of distearyl-dimethylammonium chloride and of diorganopolysiloxane containing a dimethyl itaconate functional group of Reference Example 3 | 10.0 g |
| (that is, as distearyldimethylammonium chloride | 1.0 g AS |
| and as diorganopolysiloxane | 1.0 g AS) |
| Hydroxyethyl cellulose grafted with diallyldimethylammonium chloride, sold by National Starch under the name Celquat L 200 | 0.7 g AS |
| 50/50 methacrylic acid/methyl methacrylate copolymer | 0.7 g AS |
| Perfume, preserving agent, colorant q.s. | |
| Hydrochloric acid q.s. | pH = 7 |
| Water q.s. | 100.0 g |

This composition makes wet hair easy to disentangle and endows dried hair with fullness, bounce, softness and shine.

EXAMPLE 17

A shampoo of the following composition is prepared:

| | |
|---|---|
| Aqueous emulsion containing 20% of AS obtained by dilution with hot water of a 50/50 by weight mixed melt of behenyl-trimethylammonium chloride and of diorganopolysiloxane containing a dimethyl itaconate functional group of Reference Example 3 | 4.0 g |
| (that is, as behenyltrimethylammonium chloride | 0.4 g AS |
| and as diorganopolysiloxane | 0.4 g AS) |
| Amphoteric surfactant called "Cocoamphocarboxyglycinate" in the CTFA Dictionary (3rd edition), sold by Miranol at a concentration of 38% of active substance (AS) under the name of Miranol C₂M | 10.0 g |
| Xanthan gum sold by Kelco under the name Keltrol T | 0.5 g |
| Perfume, preserving agent, colorant, q.s. | |
| Hydrochloric acid q.s. | pH = 3.5 |
| Water q.s. | 100.0 g |

This composition with good foaming properties enables wet hair to disentangle very easily. After drying, The hair is shiny soft and light.

EXAMPLE 18

A shampoo of the following composition is prepared:

| | |
|---|---|
| Aqueous emulsion containing 20% of AS obtained by dilution with hot water of a 50/50 by weight mixed melt of distearyldimethylammonium chloride and of diorganopolysiloxane containing a dimethyl itaconate functional group of Reference Example 3 | 4.0 g |
| (that is, as distearyldimethylammonium chloride and as diorganopolysiloxane | 0.4 g AS 0.4 g AS) |
| Surfactant of formula: | |

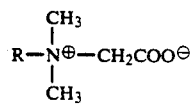

-continued

| | |
|---|---|
| R = copra radical sold at a concentration of 30% of active substance (AS) by Henkel under the name Dehyton AB 30 | 10.0 g |
| Perfume, preserving agent, colorant, q.s. | |
| Hydrochloric acid q.s. pH = 3 | |
| Water q.s. | 100.0 g |

This shampoo, with good foaming properties, endows wet hair with excellent disentangling. After drying, the hair is soft and shiny.

EXAMPLE 19

A fluid gel for hair-setting without rinsing, of the following composition is prepared:

| | |
|---|---|
| Aqueous emulsion containing 20% of AS obtained by dilution with hot water of a 50/50 by weight mixed melt of distearyldimethylammonium chloride and of diorganopolysiloxane containing a dimethyl itaconate functional group of Reference Example 3 | 0.2 g |
| (that is, as distearyldimethylammonium chloride | 0.02 g AS |
| and as diorganopolysiloxane | 0.02 g AS) |
| 50/50 methacrylic acid/methyl methacrylate copolymer | 0.7 g AS |
| Hydroxyethyl cellulose grafted with diallyldimethylammonium chloride, sold by National Starch under the name Celquat L 200 | 0.7 g AS |
| Ethyl alcohol q.s. | 10° |
| 2-Amino-2-methyl-1-propanol q.s. | pH = 7.5 |
| Perfume, colorant, preserving agent, q.s. | |
| Water q.s. | 100.0 g |

When applied to wet hair, this composition endows the hair with easy disentangling and softness. The dried hair is shiny and the hairstyle behaves well.

EXAMPLE 20

A hair-styling foam of the following composition is prepared:

| | |
|---|---|
| Aqueous emulsion containing 20% of AS obtained by dilution with hot water of a 50/50 by weight mixed melt of distearyldimethylammonium chloride and of diorganopolysiloxane containing a dimethyl itaconate functional group of Reference Example 3 | 0.2 g |
| (that is, as distearyldimethyl-ammonium chloride | 0.02 g AS |
| and as diorganopolysiloxane | 0.02 g AS) |
| Hydroxyethyl cellulose grafted with diallyldimethylammonium chloride, sold by National Starch under the name Celquat L 200 | 0.4 g |
| 82/18 methacrylic acid/hexyl methacrylate copolymer | 0.4 g AS |
| Ethyl alcohol q.s. | 10° |
| 2-Amino-2-methyl-1-propanol q.s. | pH = 7.5 |
| Perfume, colorant, preserving agent, q.s. | |
| Water q.s. | 100.0 g |
| Aerosol packaging: | |
| Above composition | 90 g |
| Freons 12/114 (57/43) | 10 g |
| Total | 100 g |

This foam is applied to washed and roughly dried hair. The latter is not rinsed and is dried. The hair disentangles easily and is soft and shiny.

EXAMPLE 21

A hair treatment cream for rinsing is prepared by melting together at about 90° C. a 50/50 weight mixture of the following two compounds:

| | |
|---|---|
| Distearyldimethylammonium chloride | 50.0 g |
| Diorganopolysiloxane containing a dimethyl itaconate functional group of Reference Example 4 | 50.0 g | which is then gradually diluted by stirring with five times its weight of hot water (at 90° C.).

A cream containing 20% of AS is obtained, whose pH is adjusted to 3.5 with HCl and an addition of perfume, preserving agent and colorant.

When applied to washed and roughly dried hair, the hair being then rinsed, this cream imparts remarkably good disentangling, much softness, shine and pliability.

EXAMPLE 22

A nonrinsed hair treatment lotion, of the following composition, is prepared:

| | |
|---|---|
| Aqueous emulsion containing 20% of AS, obtained by diluting with hot water a 50/50 by weight mixed melt of distearyldimethylammonium chloride and of diorganopolysiloxane containing a dimethyl itaconate functional group of Reference Example 2 | 0.5 g |
| (that is, expressed as distearyl-dimethylammonium chloride | 0.05 g AS |
| and as diorganopolysiloxane | 0.05 g AS) |
| Perfume, colorant, preserving agent, q.s. | |
| Triethanolamine q.s. | pH = 4.9 |
| Water q.s. | 100.0 g |

This lotion is applied to washed and roughly dried hair.

After drying, this treatment makes it easier to use the brush during blow-drying and endows hair with shine and softness.

EXAMPLE 23

A protective cream for the skin, of the following composition is prepared:

| | |
|---|---|
| Aqueous emulsion containing 20% of AS obtained by diluting with hot water a 30/70 by weight mixed melt of distearyldimethylammonium chloride and of diorganopolysiloxane containing a dimethyl itaconate functional group of Reference Example 3 | 50.0 g |
| (that is expressed as distearyl-dimethylammonium chloride | 3.0 g AS |
| and as diorganopolysiloxane | 7.0 g AS) |
| Colorant, preserving agent, perfume, q.s. | |
| Triethanolamine q.s. | pH = 4.5 |
| Water q.s. | 100.0 g |

This hydrating cream imparts softness and suppleness to skin.

We claim:

1. Silicone/water emulsion, which comprises, in an aqueous medium:
   an organopolysiloxane containing a diester functional group containing, per molecule, at least one unit of the following formula (I):

$$ZR_aSiO_{(3-a)/2} \qquad (I)$$

in which:

Z is a radical of formula:

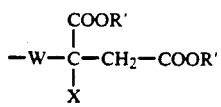

in which:
the symbols R', which are identical or different, are chosen from $C_1$-$C_{12}$ monovalent saturated hydrocarbon radicals, $C_2$-$C_{12}$ alkoxyalkyl radicals and $C_6$-$C_{12}$ aryl, alkylaryl and arylalkyl radicals;
the symbol X is chosen from a hydrogen atom and the methyl radical;
the symbol W is chosen from a covalent bond and a linear or branched alkylene radical containing from 1 to 4 carbon atoms;
the symbols R, which are identical or different, are chosen from $C_1$-$C_{20}$ alkyl, vinyl, phenyl and 3,3,3-trifluoropropyl or hydroxyl radicals, on condition that only one of the radicals R per silicon atom is a hydroxyl; and
a is chosen from 0, 1 and 2;
an effective quantity, for forming an emulsion, of at least one emulsifier chosen from anionic, cationic, amphoteric and nonionic surface-active agents.

2. Emulsion according to claim 1, wherein the anionic surface-active agents are chosen from alkali metal alkylbenzenesulphonates, alkyl sulphates, alkyl ether sulphates, alkylaryl ether sulphates and dioctylsulphosuccinates.

3. Emulsion according to claim 1, wherein the cationic surface-active agents are chosen from quaternary ammonium halides and polyethoxylated quaternary ammonium salts.

4. Emulsion according to claim 1, wherein the amphoteric surface-active agents are chosen from N-alkyl-($C_{10}$-$C_{22}$)betaines, N-alkyl($C_{10}$-$C_{22}$)sulphobetaines, N-alkyl-($C_{10}$-$C_{22}$)amidobetaines, alkyl($C_{10}$-$C_{22}$)imidazolines and asparagine derivatives.

5. Emulsion according to claim 1, wherein the nonionic surface-active agents are chosen from polyethoxylated fatty acids, sorbitan esters, polyethoxylated sorbitan esters, polyethoxylated alkylphenols, polyethoxylated fatty alcohols, polyethoxylated or polyglycerolated fatty amides and polyglycerolated alcohols and α-diols.

6. Emulsion according to claim 1, wherein in formula (I) the symbols W and X are chosen from:

W is $CH_2$ and X is H;

W is —$(CH_2)_3$— and X is H;

W is —$CH_2$—CH—$CH_2$— and X is H; and
            |
            $CH_3$

W is a valency bond and X is methyl.

7. Emulsion according to claim 1, which comprises:
100 parts by weight of the organopolysiloxane containing a diester functional group;
1 to 300 parts by weight of at least one surface-active agent; and
5 to 2000 parts of water.

8. Dermatological composition, which is presented in the form of a silicone/water aqueous emulsion as defined in claim 1 and which additionally contains a dermatologically active substance.

9. Process for the cosmetic or dermatological treatment of hair or of the skin comprising the use of an emulsion as defined in claim 1.

10. Emulsion according to claim 1, wherein the organopolysiloxane containing a diester functional group is chosen from those of formula:

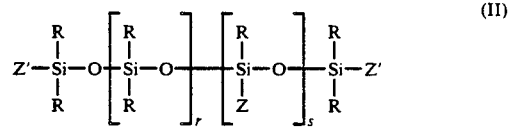

in which:
the symbols R and Z have the meaning given in claim 1;
the symbols Z', which are identical or different, are chosen from radicals R and Z;
r is an integer between 0 and 500 inclusive; and
s is an integer chosen between 0 and 50 inclusive and, if s is 0, at least one of the two symbols Z' is Z;
and those of formula:

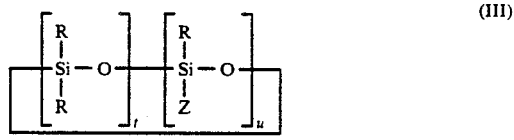

in which:
R and Z have the same meaning as in claim 1;
u is an integer between 1 and 20 inclusive;
t is an integer between 0 and 20 inclusive; and
t+u is greater than or equal to 3.

11. Emulsion according to claim 10, wherein the formula of the orgnaosiloxne containing a diester functional group:
R and R' are methyl;
r is between 5 and 50 inclusive;
s is an integer between 1 and 20 inclusive; and
t+u is between 3 and 10 inclusive.

12. Cosmetic composition intended for the treatment of hair or of the skin and presented in the form of a silicone/water aqueous emulsion, wherein the emulsion is as defined in claim 1.

13. Composition according to claim 12 which is employed as a shampoo; as a conditioning product; as a rinsing product which can be applied after shampooing, before or after dyeing and bleaching, before or after permanent-waving or straightening; as hair-setting or blow-drying lotions; as a restructuring composition; or as an additive to permanent-waving.

14. Composition according to claim 12, which also contains a cosmetically acceptable solvent chosen from $C_1$-$C_4$ alcohols.

15. Composition according to claim 12, which additionally contains at least one cosmetically acceptable adjuvant chosen from perfumes, colorants, preserving agents, hydrating products, sequestering agents, sunscreening agents, foaming agents, conditioning agents, thickening agents, foam stabilizers and propellants.

16. Composition according to claim 12, which additionally contains at least one cationic polymer and at least one anionic polymer having a molecular weight of between 500 and 3,000,000.

17. Composition according to claim 12, in which the PH is adjusted to between 3 and 10.

18. Composition according to claim 12, which contains thickeners chosen from xanthan gum, guar gum or its derivatives, gum arabic or carob gum, sodium alginate, cellulose derivatives, polyacrylic acid derivatives, mixtures of phosphoric acid and of amides; or else the product resulting from the ionic interaction of a cationic polymer consisting of a copolymer of cellulose or of a cellulose derivative grafted with a quaternary ammonium salt of a water-soluble monomer and of a carboxylic anionic polymer with an absolute capillary viscosity equal to or lower than $30 \times 10^{-3}$ Pa s in dimethylformamide or methanol at a concentration of 5% and at 30° C.

19. Process for a cosmetic treatment of hair or of the skin, wherein at least one composition such as defined in claim 12 is applied to the hair or to the skin.

20. Composition according to claim 12, which comprises:
(i) at least one organopolysiloxane containing a diester functional group containing, per molecule, at least one unit of formula:

$$ZR_aSiO_{(3-a)/2} \quad (I)$$

in which:
Z is a radical of formula:

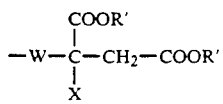

in which:
the symbols R', which are identical or different, are chosen from $C_1$–$C_{12}$ monovalent saturated hydrocarbon radicals, $C_2$–$C_{12}$ alkoxyalkyl radicals and $C_6$–$C_{12}$ aryl, alkylaryl and arylalkyl radicals;
the symbol X is chosen from a hydrogen atom and the methyl radical;
the symbol W is chosen from a covalent bond and a linear or branched alkylene radical containing from 1 to 4 carbon atoms; and
the symbols R, which are identical or different, are chosen from $C_1$–$C_{20}$ alkyl, vinyl, phenyl and 3,3,3-trifluoropropyl or hydroxy radicals, on condition that only one of the radicals R per silicon atom is a hydroxyl;
(ii) and at least one quarternary ammonium halide containing at least one $C_{10}$–$C_{30}$ fatty chain.

21. Composition according to claim 20, wherein the quarternary ammonium halide is chosen from distearyldimethylammonium chloride and behenyltrimethylammonium chloride.

22. Composition according to claim 20 which comprises 0.01% to 15% by weight of said quarternary ammonium halide and 0.01% to 15% by weight of said diorganopolysiloxane containing one unit of formula (I) per molecule.

23. Composition according to claim 20 comprising 0.02% to 10% by weight of said quarternary ammonium halide and 0.02% to 10% by weight of said diorganopolysiloxane.

* * * * *